United States Patent
Ross, Jr. et al.

(10) Patent No.: US 9,604,942 B2
(45) Date of Patent: Mar. 28, 2017

(54) PREPARATION OF HALOALKOXYARYLHYDRAZINES AND INTERMEDIATES THEREFROM

(71) Applicant: Dow AgroSciences LLC, Indianapolis, IN (US)

(72) Inventors: Ronald Ross, Jr., Zionsville, IN (US); Gary Roth, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/725,276

(22) Filed: May 29, 2015

(65) Prior Publication Data

US 2015/0259303 A1  Sep. 17, 2015

Related U.S. Application Data

(63) Continuation of application No. 14/192,412, filed on Feb. 27, 2014, now Pat. No. 9,108,932.

(60) Provisional application No. 61/778,475, filed on Mar. 13, 2013.

(51) Int. Cl.
  *C07D 249/08* (2006.01)
  *C07C 243/22* (2006.01)
  *C07C 249/02* (2006.01)

(52) U.S. Cl.
  CPC .......... *C07D 249/08* (2013.01); *C07C 243/22* (2013.01); *C07C 249/02* (2013.01)

(58) Field of Classification Search
  CPC .................................................. C07D 249/08
  See application file for complete search history.

(56) References Cited

U.S. PATENT DOCUMENTS

| | | |
|---|---|---|
| 5,187,185 A | 2/1993 | Outcalt et al. |
| 5,304,657 A | 4/1994 | Toki et al. |
| 5,726,324 A | 3/1998 | Huang et al. |
| 6,166,243 A | 12/2000 | Jin et al. |
| 6,258,973 B1 | 7/2001 | D'Silva et al. |
| 6,392,081 B1 | 5/2002 | Ancel |
| 6,410,737 B1 | 6/2002 | Ancel et al. |
| 6,417,187 B2 | 7/2002 | Hegde et al. |
| 7,094,906 B2 | 8/2006 | Ancel |
| 7,323,574 B2 | 1/2008 | Ancel et al. |
| 2005/0009834 A1 | 1/2005 | Itoh et al. |
| 2007/0259962 A1 | 11/2007 | Deyn et al. |
| 2008/0199606 A1 | 8/2008 | Karl et al. |
| 2012/0053216 A1 | 3/2012 | Creemer et al. |
| 2012/0172218 A1 | 7/2012 | Crouse et al. |
| 2013/0030190 A1 | 1/2013 | Gharda |

OTHER PUBLICATIONS

PCT International Search Report/Written Opinion for PCT/US2014/018989, completed May 23, 2014.

*Primary Examiner* — Shawquia Jackson
(74) *Attorney, Agent, or Firm* — Yung H. Lee; Carl D. Corvin; Barnes & Thornburg LLP

(57) ABSTRACT

The invention in this document is related to the field of preparation of haloalkoxyarylhydrazines and certain intermediates derived therefrom, where said intermediates are useful in the preparation of certain pesticides disclosed in U.S. Pat. No. 8,178,658.

20 Claims, No Drawings

PREPARATION OF HALOALKOXYARYLHYDRAZINES AND INTERMEDIATES THEREFROM

CROSS REFERENCE TO RELATED APPLICATIONS

This application is a continuation of U.S. application Ser. No. 14/192,412 filed on Feb. 27, 2014, which claims the benefit of U.S. Provisional Patent Application Ser. No. 61/778,475 filed Mar. 13, 2013, the entire disclosures of which are hereby expressly incorporated by reference.

FIELD OF THE DISCLOSURE

This document is related to the field of preparation of haloalkoxyarylhydrazines and intermediates therefrom, where said intermediates are useful in the preparation of certain pesticides.

BACKGROUND OF THE DISCLOSURE

U.S. Pat. No. 8,178,658 discloses pesticidal compositions comprising a compound having the following structure:

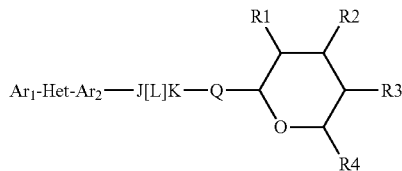

Formula A-1 wherein $Ar_1$, Het, $Ar_2$, J, L, K, Q, R1, R2, R3, and R4 are disclosed in the patent. While processes are disclosed on how to make such compounds, and such processes are useful, it is desired to have more useful processes to make these compounds. In particular, it is desirable to have more commercially useful routes to certain substituted triaryl intermediates disclosed in the patent that are useful in producing the compounds of Formula A-1.

Description of the Disclosure

Throughout this document, all temperatures are given in degrees Celsius, and all percentages are weight percentages unless otherwise stated.

Scheme 1

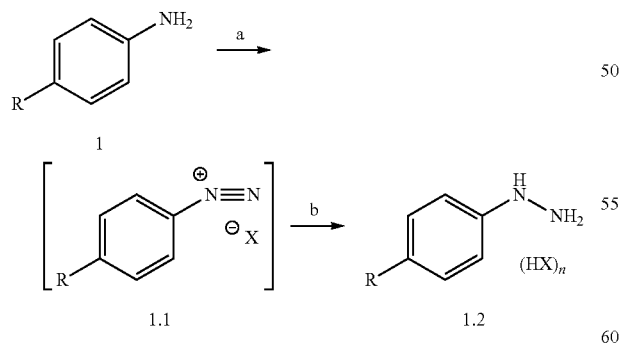

Haloalkoxyarylhydrazines of Formula 1.2, wherein R is a $(C_1-C_6)$haloalkoxy, such as, but not limited to, trifluoromethoxy and pentafluoroethoxy, can be prepared as illustrated in Scheme 1. In general, in step a, a haloalkoxyaniline of Formula 1 is reacted with sodium nitrite ($NaNO_2$) to produce an intermediate diazonium salt of Formula 1.1. In step b, the intermediate diazonium salt is reduced to form haloalkoxyarylhydrazines of Formula 1.2.

In Step a, approximately a 1:1 molar ratio of the haloalkoxyaniline and $NaNO_2$ may be used, however, molar ratios of about 1:2 may also be used. This reaction is conducted in a polar, protic solvent. Suitable examples of polar, protic solvents are water, formic acid, n-butanol, isopropanol, ethanol (EtOH), methanol (MeOH), acetic acid (AcOH), or mixtures thereof. Currently, it is preferred if water is used. Furthermore, Step a is conducted in the presence of an inorganic acid. Suitable examples are hydrochloric acid (HCl), nitric acid ($HNO_3$), phosphoric acid ($H_3PO_4$), sulphuric acid ($H_2SO_4$), boric acid ($H_3BO_3$), hydrofluoric acid (HF), hydrobromic acid (HBr), perchloric acid ($HClO_4$), tetrafluoroboric acid ($HBF_4$), or mixtures thereof. Currently, it is preferred if HCl is used. The pH of the reaction is from about −1 to about 4, preferably from about −1 to about 1. The reaction is conducted at a temperature from about −10° C. to about 5° C. and preferably from about −5° C. to about 5° C. The reaction is conducted at about atmospheric pressure, however, higher or lower pressures can be used.

Step b is conducted in a polar, protic solvent. Suitable examples of polar, protic solvents are water, formic acid, n-butanol, isopropanol, nitromethane, EtOH, MeOH, AcOH, or mixtures thereof. Currently, it is preferred if water is used. This reaction is conducted in the presence of a reducing agent, such as, for example, sodium dithionite ($Na_2S_2O_4$), tin (II) chloride ($SnCl_2$), hydrogen, and ammonium formate. The pH of the reduction reaction mixture is from about 8 to about 14, and preferably from about 9 to about 12. The reaction is conducted at a temperature from about −10° C. to about 10° C. preferably about −5° C. to about 5° C. The reaction is conducted at about atmospheric pressure, however, higher or lower pressures can be used.

If desired, the haloalkoxyarylhydrazines can be obtained as a salt or a free base ($(HX)_n$ where n=0, 1, or 2) with pH adjustments following the reaction in step b.

A particularly preferred haloalkoxyarylhydrazine of Formula 1.2. is

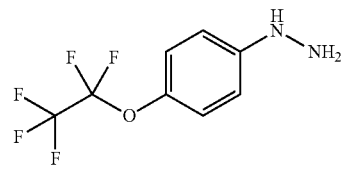 [SMILES: NNc1ccc(OC(F)(F)C(F)(F)F)cc1]

(4-(perfluoroethoxy)phenyl)hydrazine

Scheme 2

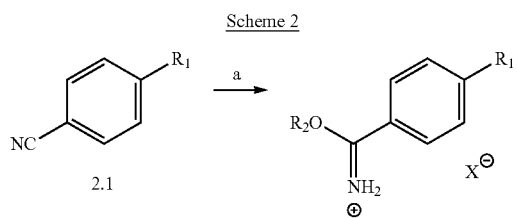

Arylalkoxyimidate salts of Formula 2.2, wherein $R_1$ is $NO_2$, C(=O)OH or a $(C_1-C_6)$ ester thereof (C(=O)O($C_1$-$C_6$)alkyl), for example, methyl (C(=O)OCH_3) or ethyl ester (C(=O)OCH₂CH₃), can be prepared as outlined in Scheme 2. In step a, benzonitriles of Formula 2.1 are reacted with anhydrous inorganic acids in an alcohol to produce said arylalkoxyimidate salts, wherein $R_2$ is $(C_1\text{-}C_6)$alkyl.

In Step a benzonitriles of Formula 2.1 are treated with an anhydrous inorganic acid (HX, wherein X is F, Cl, Br, or I, preferably Cl or Br), for example, HCl or HBr in a polar protic solvent, for example, an alcohol ($R_2OH$), for example, MeOH, EtOH, n-butanol, isopropanol, or mixtures thereof. In some embodiments, HX gas is introduced directly into a solution of the benzonitrile of Formula 2.1 in $R_2OH$ via a sparge tube. The reaction is conducted at a temperature from about −10° C. to about −5° C. and preferably from about 0° C. to about −5° C. during the HX sparge. It is preferred if the temperature is raised to about 25° C. following the addition of the HX. HX gas may be introduced into the reaction system at pressures ranging from about atmospheric pressure to about 3500 kPa. Alternatively, solutions of benzonitriles of Formula 2.1, in a variety of organic solvents, for example, tetrahydrofuran (THF), ethyl acetate (EtOAC), dichloromethane (CH₂Cl₂), toluene, or mixtures thereof, are treated with an anhydrous inorganic acid (HX), for example, HCl or HBR, in the presence of an alcohol ($R_2OH$). Molar ratios of benzonitriles of Formula 2.1 to the alcohol are from about 1:1 to about 1:10, however, molar ratios of about 1:1000 to about 1000:1 may also be used. In another embodiment, HX is generated in situ via the decomposition of an acyl halide, such as, for example, acetyl chloride and acetyl bromide, when said acyl halide is contacted with $R_2OH$. In another embodiment thionyl chloride is used as a source of HCl. In this method the acyl halide may be added to a solution of the benzonitrile of Formula 2.1 in $R_2OH$ or may be added to the $R_2OH$ first, followed by the addition of the benzonitrile of Formula 2.1 to the pre-formed solution of HX. In both cases, the reaction is conducted at a temperature from about −10° C. to about −5° C. and preferably from about 0° C. to about −5° C. during the HX formation, and preferably the temperature is raised to about 25° C. following the addition.

In some embodiments, subjecting benzonitriles of Formula 2.1, wherein $R_1$ is nitro or a carboxylate ester, to one of the described methods affords alkoxyimidate salts of Formula 2.2, wherein $R_1$ is as defined and $R_2$ is derived from $R_2OH$. In another embodiment, subjecting benzonitriles of Formula 2.1, wherein $R_1$ is a carboxylic acid, to one of the described methods affords alkoxyimidate salts of Formula 2.2, wherein $R_1$ is a mixture of the carboxylic acid and ester, wherein the $R_1$ ester and $R_2$ are both derived from $R_2OH$, e.g., when $R_2OH$ is MeOH, $R_1$ is the methyl ester and $R_2$ is the methylimidate.

Scheme 3

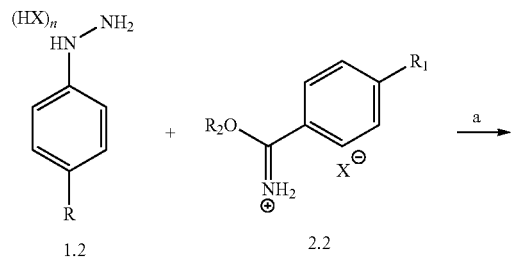

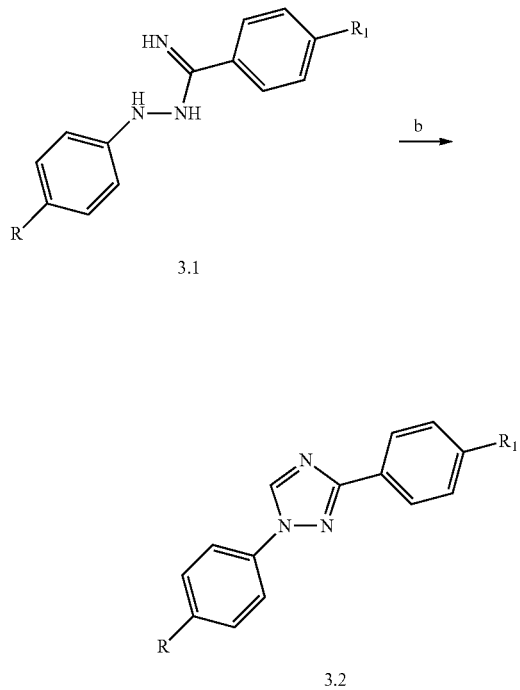

1,3-diaryltriazoles of Formula 3.2 can be prepared as illustrated in Scheme 3. In step a, haloalkoxyarylhydrazine of Formula 1.2 is reacted with arylalkoxyimidate of Formula 2.2 to produce an intermediate iminohydrazine of Formula 3.1. In step b, the iminohydrazine is cyclized using a formate source, such as, for example, formic acid, formate esters, such as methyl- and ethyl formate, and orthoesters, such as, trimethyl- and triethyl orthoformate, to afford said 1,3-diaryltriazoles of Formula 3.2.

In step a, solutions of arylalkoxyimidate salts of Formula 2.2 in a weakly alkaline, heterocyclic solvent, such as pyridine, lutidine, or mixtures thereof, or in a non-basic, polar, aprotic solvent such as, for example, acetonitrile (MeCN) and THF, in the presence of organic or inorganic bases are reacted with haloalkoxyarylhydrazine salts ((HX)$_n$ where n=0, 1, or 2) of Formula 1.2 to produce an intermediate iminohydrazine of Formula 3.1. Suitable examples of organic and inorganic bases are pyridine, trialkylamines, such as, trimethylamine, triethylamine (TEA), and diisopropylethylamine (DIPEA), and alkali carbonates, such as, sodium- (Na₂CO₃) and potassium carbonate (K₂CO₃), respectively. The reaction is conducted at a temperature from about −10° C. to about −10° C. and preferably from about 0° C. to about −5° C. during the addition of the hydrazine, and then the temperature is preferably raised to about 25° C. following the addition.

In step b, the intermediate iminohydrazine of Formula 3.1 is cyclized using a formate source. The reaction is conducted at a temperature from about 20° C. to about 100° C. and preferably from about 95° C. to about 100° C., which effectively enables cyclization to form the 1,3-diaryltriazole of Formula 3.2.

Scheme 4

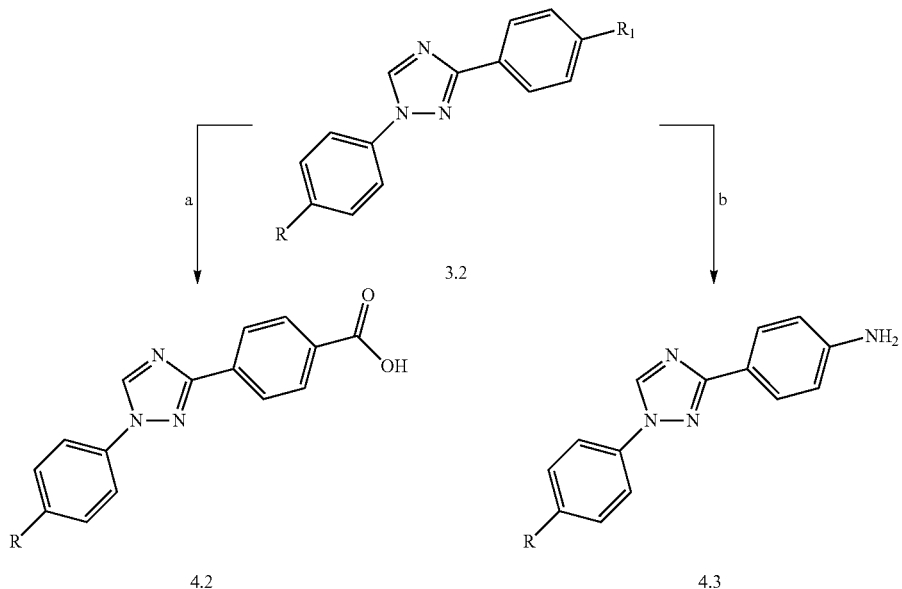

1,3-diaryl triazole compounds of Formula 4.2 and Formula 4.3 can be prepared according to Scheme 4. In method a, intermediate 1,3-diaryltriazoles of Formula 3.2, wherein $R_1$ is an ester, can be saponified to give 1,3-diaryltriazoles substituted with a carboxylic acid of Formula 4.2. In method b, intermediate 1,3-diaryltriazole of Formula 3.2), wherein $R_1$ is nitro, can be reduced to give 1,3-diaryltriazoles substituted with an amine of Formula 4.3.

Method a can be conducted in a polar, protic solvent, such as an alcohol, for example, MeOH, EtOH, n-butanol, isopropanol, or mixtures thereof, or in a polar, aprotic solvent such as THF, in the presence of an alkali hydroxide base, such as, for example, sodium (NaOH), potassium (KOH), or lithium hydroxide (LiOH), and water. The reaction can be conducted at a temperature from about 20° C. to about 60° C. and preferably from about 20° C. to about 30° C. The pH of the reaction mixture is from about 8 to about 14 and preferably from about 10 to about 12.

Method b can be carried out in a wide variety of organic solvents including, for example, polar, protic solvents, such as alcohols, such as, MeOH, EtOH, n-butanol, isopropanol, or mixtures thereof, polar, aprotic solvents, such as THF and EtOAC, or organic acids, such as, for example, AcOH, in the presence of a catalyst, such as palladium on carbon or palladium hydroxide on carbon, and a hydrogen source, such as, for example hydrogen gas, ammonium salts, such as, ammonium formate, and cyclohexadiene. The reaction can be conducted at a temperature from about 20° C. to about 50° C. and preferably from about 20° C. to about 30° C. The reaction can be conducted at a pressure from about 101 kPa to about 689 kPa and preferably from about 101 to about 345 kPa. See also WO 2009/102736 A1.

1,3-diaryltriazole of Formula 4.2 and Formula 4.3 can be used as intermediates to form pesticides disclosed in U.S. Pat. No. 8,178,658 as disclosed therein.

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz, and $^{13}$C NMR spectral data are in ppm (δ) and were recorded at 75, 100 or 150 MHz, unless otherwise stated.

Example 1

Preparation of (4-(perfluoroethoxy)phenyl)hydrazine

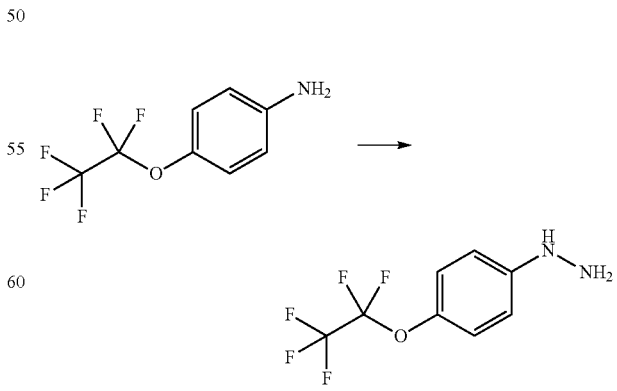

To a dry 500 mL round bottomed flask equipped with magnetic stirrer, nitrogen inlet, addition funnel, and thermometer, were charged 4-perfluoroethoxyaniline (11.8 g, 52.0 mmol) and HCl (2 N, 100 mL), and the resulting suspension was cooled to about 0° C. with an external ice/salt (sodium chloride, NaCl) bath. To the suspension was added a solution of NaNO$_2$ (1.05 g, 54.5 mmol) in water (10 mL) dropwise from the addition funnel at a rate which maintained the temperature below 5° C., and the resulting colorless solution was stirred at 0° C. for 30 minutes (min). To a separate 500 mL round bottom flask equipped with magnetic stir bar, addition funnel, and thermometer were added Na$_2$S$_2$O$_4$ (27.1 g, 156 mmol), NaOH (1.04 g, 26.0 mmol), and water (60 mL), and the suspension was cooled to about 5° C. with an external cooling bath. The diazonium salt solution prepared in round bottom 1 was transferred to the addition funnel and added to round bottom 2 at a rate which maintained the temperature below 8° C. Following the addition, the reaction mixture was warmed to 18° C. and the pH was adjusted to about 8 with 50% NaOH. The resulting pale orange solution was extracted with EtOAC (3×100 mL) and the combined organic extracts were washed with water (100 mL), washed with saturated aqueous NaCl solution (100 mL), dried over anhydrous magnesium sulfate (MgSO$_4$), filtered, and the filtrate concentrated to give the crude product as an orange semi-solid (12.2 g). The residue was purified by flash column chromatography using 0-100% (v/v) EtOAc/hexanes as eluent to give the title compound as a yellow liquid (10.4 g, 83%): $^1$H NMR (400 MHz, CDCl$_3$) δ 7.18-7.00 (m, 2H), 6.97-6.68 (m, 2H), 5.24 (bs, 1H), 3.98-3.09 (bs, 2H); $^{19}$F NMR (376 MHz, CDCl$_3$) δ −86.00, −86.01, −87.92; EIMS m/z 242 [M$^+$].

Example 2

Preparation of methyl 4-(imino(methoxy)methyl)benzoate hydrochloride

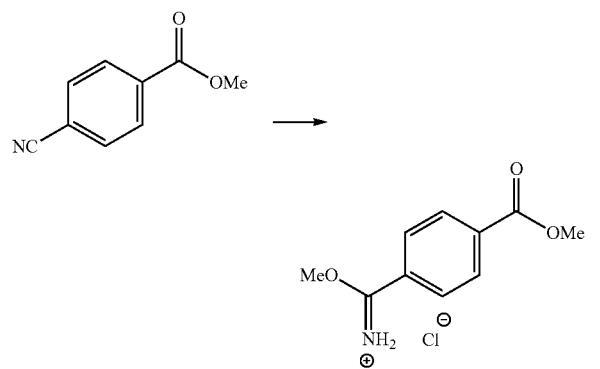

To a magnetically stirred solution of methyl 4-cyanobenzoate (12.5 g, 78 mmol) in benzene (25 mL) and MeOH (7 mL) cooled to 0° C. was bubbled anhydrous HCl subsurface for 3 hours (h). After storing in the refrigerator overnight, a heavy white precipitate formed. The solid was filtered through a fritted glass funnel and washed with diethyl ether to furnish the title compound as a white solid (17.5 g, 96%): mp 209-210° C.; $^1$H NMR (400 MHz, CDCl$_3$) δ 13.05 (br s, 1H), 12.32 (br s, 1H), 8.48 (m, 2H), 8.22 (m, 2H), 4.60 (s, 3H), 3.97 (s, 3H); $^{13}$C NMR (101 MHz, DMSO-d$_6$) δ 166.98, 165.69, 138.38, 131.74, 129.00, 127.78, 52.29, 26.16; EIMS m/z 192 [M$^+$].

Example 3

Preparation of methyl 4-(ethoxy(imino)methyl)benzoate hydrochloride

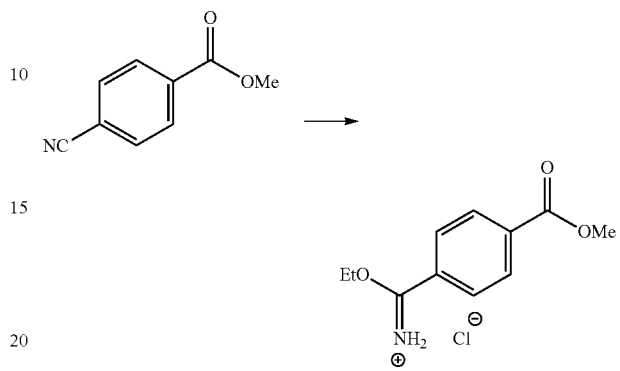

A 2 L, three-necked round bottomed flask equipped with a magnetic stir bar, a temperature probe, addition funnel and nitrogen inlet was charged with methyl 4-cyanobenzoate (100 g, 620 mmol). The methyl 4-cyanobenzoate was dissolved in EtOH (438 mL) and cooled in an ice bath to 0° C. Acetylchloride (353 mL, 4960 mmol) was added dropwise into the stirring solution over a 2 h period during which time an exotherm from 0° C. to 21° C. was noted. The reaction-flask was capped, sealed with Parafilm®, and allowed to stir at 23° C. for 18 h. The resulting white solid was collected by vacuum filtration and washed with EtOH. The filtrate was concentrated until it became turbid and was then cooled in an ice bath. The resulting precipitate was collected by vacuum filtration, rinsed with EtOH, and the filtrate treated as described to give another crop. The solids were dried to give the title compound as a white solid (128 g, 85%): $^1$H NMR (400 MHz, CDCl$_3$) δ 12.85 (br s, 1H), 12.20 (br s, 1H), 8.49 (m, 2H), 8.23 (m, 2H), 5.00 (q, 2H), 4.00 (s, 3H), 1.72 (t, 3H).

Example 4

Preparation of 4-(ethoxy(imino)methyl)benzoic acid hydrochloride and ethyl 4-(ethoxy(imino)methyl)benzoate hydrochloride

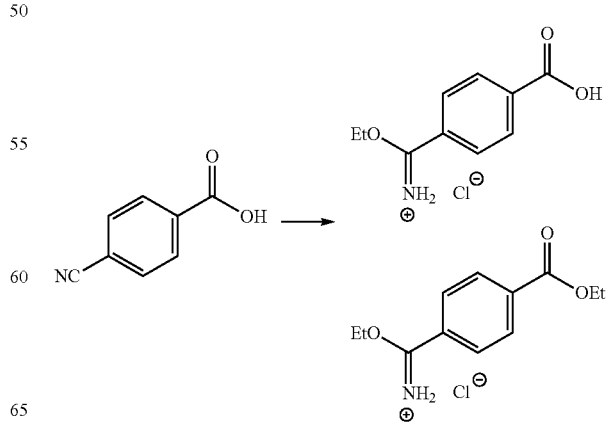

A 500 mL, three-necked flask, equipped with a magnetic stir bar, nitrogen inlet, addition funnel, and a temperature probe was charged with anhydrous EtOH (125 mL). The vessel was cooled to 5° C. and acetyl chloride (97 mL, 1332 mmol) was added at a rate that maintained the temperature range of 5 to 10° C. When the addition was complete, 4-cyanobenzoic acid (25 g, 167 mmol) was added in portions over 15 min. No exotherm was noted during the addition of the solid. When the addition was complete, the white suspension was allowed to warm to 25° C. The reaction vessel was sealed with Parafilm® and stirred at 23° C. for 18 h. The white suspension was vacuum filtered and the solid was rinsed with EtOH and dried to constant mass, furnishing 4-(ethoxy(imino)methyl)benzoic acid hydrochloride as a white solid (25 g, 65%): $^1$H NMR (400 MHz, DMSO-$d_6$) δ 12.44 (br s, 1H), 8.26 (m, 2H), 8.14 (m, 2H), 4.70 (q, 2H), 1.51 (t, 3H). The filtrate was concentrated and treated with ether to give a white solid. The solid was collected by vacuum filtration and rinsed with ether to give ethyl 4-(ethoxy(imino)methyl)benzoate hydrochloride as a white solid (11 g, 25%): $^1$H NMR (400 MHz, DMSO-$d_6$) δ 12.07 (br s, 1H), 8.24 (m, 2H), 8.15 (m, 2H), 4.66 (q, 3H), 4.37 (q, 3H), 1.49 (t, 3H), 1.35 (q, 3H).

Example 5

Preparation of ethyl 4-nitrobenzimidate hydrochloride

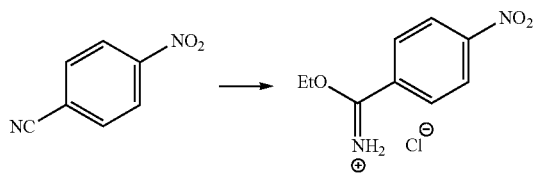 [SMILES: N#Cc1ccc([N+](=O)[O-])cc1 ; CCOC(=[NH2+])c1ccc([N+](=O)[O-])cc1 ; [Cl-]]

To a solution of 4-nitrobenzonitrile (27 g, 182 mmol) in EtOH (128 ml, 2187 mmol) under nitrogen was added acetyl chloride (104 ml, 1458 mmol) dropwise at 0° C. over 1 h, and the reaction was warmed to room temperature. The flask was sealed and the reaction was stirred for 56 h. The resulting precipitate (4-nitrobenzamide) was collected by filtration, and the filtrate was treated with diethyl ether. The resulting precipitate was collected by filtration, washed with diethyl ether and air dried to give the title compound (26.7 g, 58%): mp 198-200° C.; $^1$H NMR (400 MHz, DMSO-$d_6$) δ 8.37-8.30 (m, 2H), 8.21-8.13 (m, 2H), 7.35 (s, 1H), 7.22 (s, 1H), 7.09 (s, 1H), 4.34 (q, J=7.1 Hz, 2H), 1.32 (t, J=7.1 Hz, 3H); EIMS m/z 193 [M$^+$].

Example 6

Preparation of methyl 4-(1-(4-(trifluoromethoxy)phenyl)-1H-1,2,4-triazol-3-yl)benzoate

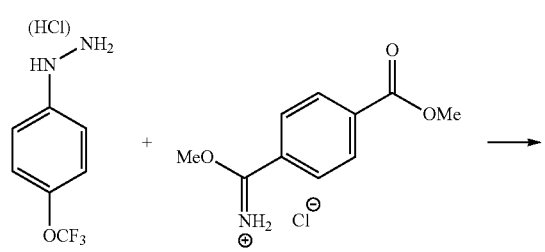

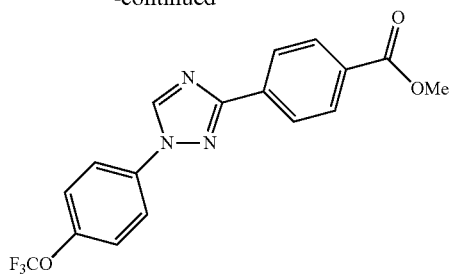

To a magnetically stirred solution of methyl 4-(imino(methoxy)methyl)benzoate hydrochloride (1.15 g, 5.00 mmol) in anhydrous pyridine (5 mL) cooled by an ice bath was added (4-(trifluoromethoxy)phenyl)hydrazine hydrochloride (1.14 g, 5.00 mmol) in several portions. After warming to room temperature overnight (18 h), the yellow reaction mixture was diluted with water (25 mL) and washed with CH$_2$Cl$_2$ (2×50 mL). The combined organic layers were washed with brine, dried over MgSO$_4$, filtered, and concentrated to give an orange-yellow solid (1.60 g). The solid was dissolved in formic acid (15 mL), warmed to reflux, and stirred at reflux for 8 h. The reaction mixture was cooled to room temperature, diluted with water, and washed with diethyl ether (2×50 mL). The combined diethyl ether washes were washed with water (3×50 mL), washed with brine (50 mL), dried over MgSO$_4$, filtered, and concentrated on a rotary evaporator to give the title compound as a tan solid (1.42 g, 78%). A sample was purified for analytical characterization by flash chromatography using 0-100% (v/v) EtOAc/hexanes as eluent to give the product as an off-white solid: mp 171-172° C.; $^1$H NMR (400 MHz, CDCl$_3$) δ 8.60 (s, 1H), 8.27 (m, 2H), 8.15 (m, 2H), 7.81 (m, 2H), 7.40 (d, J=8.5 Hz, 2H), 3.95 (s, 3H); $^{13}$C NMR (101 MHz, CDCl$_3$) δ 166.76, 162.61, 148.55, 141.77, 135.41, 134.46, 131.03, 130.02, 126.46, 122.44, 121.66, 121.31, 119.10; EIMS m/z 363 [M$^+$].

Example 7

Preparation of 4-(1-(4-(perfluoroethoxy)phenyl)-1H-1,2,4-triazol-3-yl)benzoic acid

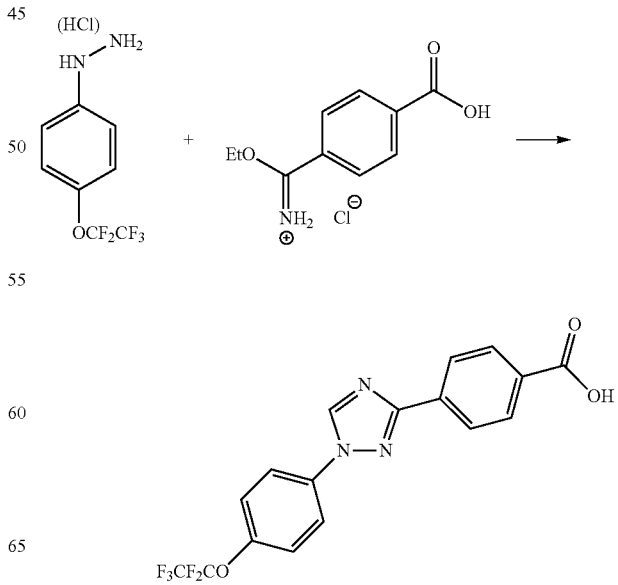

A 1 liter (L), three-neck round bottom flask, equipped with an overhead mechanical stirrer, temperature probe, and nitrogen inlet was charged with 4-(ethoxy(imino)methyl) benzoic acid hydrochloride (25 g, 109 mmol) and pyridine (200 mL). The white suspension was cooled to 5° C. in anice bath and (4-(perfluoroethoxy)phenyl)hydrazine hydrochloride (30.9 g, 109 mmol) was added in portions. The white suspension turned yellow and the temperature rose to 5.7° C. The ice bath was removed and the reaction mixture was allowed to warm slowly. At about 12° C., the contents of the flask became too thick to sir. Additional pyridine (20 mL) was added and warming continued for 20 min. The reaction mixture was poured into water (400 mL) resulting in precipitation of a flocculent solid. The mixture was extracted with CH$_2$Cl$_2$ (1×400 mL) and the phases were separated. The residual solid floating on top of the aqueous layer was collected by vacuum filtration and washed with CH$_2$Cl$_2$, and the aqueous filtrate was extracted with CH$_2$Cl$_2$ (2×200 mL). The organic extracts and washes were combined, washed with water (2×500 mL), and the water washes were back-extracted with CH$_2$Cl$_2$ until the aqueous layer was colorless (1×200 mL). The organic extracts were concentrated under reduced pressure to yield a dark, red oil (17.2 g). The previously isolated solid was suspended in CH$_2$Cl$_2$ (500 mL), stirred for 5 min, collected by filtration, rinsed on the filter with CH$_2$Cl$_2$, and dried under vacuum at 50° C. to give a bright yellow solid (20 g).

A 500 mL, three-necked, round bottom flask, fitted with a magnetic stir bar, temperature probe, and nitrogen inlet, was charged with the dark red oil (17.2 g) and the bright yellow solid (20 g) isolated above. Formic acid (200 mL) was added and the mixture was heated to 100° C. and stirred for 16 h. The heat was removed and the mixture was allowed to cool. The mixture was cooled to 23° C. (precipitate forms at about 90° C.) and water (200 mL) was added. The mixture was stirred for 1 h and the solid was collected by vacuum filtration, washed with water, air dried, and then dried under vacuum at 50° C. for 2 days (d) to furnish the title compound as a light tan solid (22.3 g, 51%): $^1$H NMR (400 MHz, DMSO-d$_6$) δ 13.13 (s, 1H), 9.48 (s, 1H), 8.23 (m, 2H), 8.10 (m, 4H), 7.64 (m, 2H).

Example 8

Preparation of 3-(4-nitrophenyl)-1-(4-(perfluoroethoxy)phenyl)-1H-1,2,4-triazole

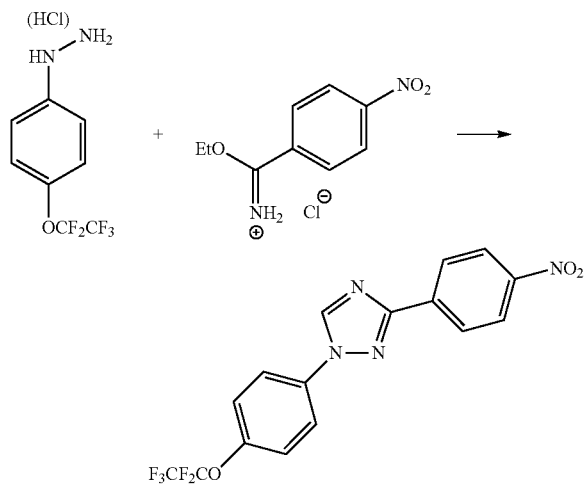

To a stirred solution of ethyl 4-nitrobenzimidate hydrochloride (3 g, 13 mmol) in pyridine (13 mL) at 0° C. was added (4-(perfluoroethoxy)phenyl)hydrazine hydrochloride (3.62 g, 13.0 mmol) in three portions. The reaction mixture was warmed to room temperature and stirred for 2 h and was diluted with water and CH$_2$Cl$_2$. The phases were separated and the aqueous layer was extracted with CH$_2$Cl$_2$ (3×20 mL), and the combined organic fractions were washed with water (30 mL), dried over MgSO$_4$, and filtered. Concentration of the filtrate afforded a sticky red solid: $^1$H NMR (400 MHz, CDCl$_3$) δ 8.34-8.23 (m, 2H), 8.00-7.90 (m, 2H), 7.20-7.07 (m, 4H), 6.33 (s 1H), 4.66 (s, 2H); ESIMS m/z 390 ([M]$^+$).

The solid was added to formic acid (30 mL) and the reaction was heated to 100° C. and stirred for 18 h. The reaction mixture was cooled to room temperature and added to cold water. The resulting precipitate was collected by vacuum filtration, washed with water, and dried under vacuum to give the title compound (4.99 g, 96%) as a light pink solid: mp 132-135° C.; $^1$H NMR (400 MHz, CDCl$_3$) δ 8.68 (s, 1H), 8.43-8.31 (m, 4H), 7.89-7.80 (m, 2H), 7.49-7.38 (m, 2H); ESIMS m/z 400 ([M]$^+$).

Example 9

Preparation of 4-(1-(4-(trifluoromethoxy)phenyl)-1H-1,2,4-triazol-3-yl)benzoic acid

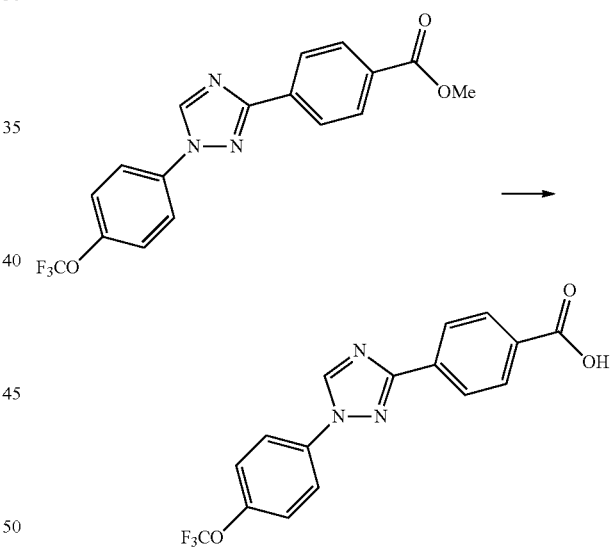

To a solution of methyl 4-(1-(4-(trifluoromethoxy)phenyl)-1H-1,2,4-triazol-3-yl)benzoate (0.332 g, 0.914 mmol) in THF (6 mL) and water (3 mL) was added LiOH (0.066 g, 2.74 mmol), and the solution immediately turned from yellow to orange-red. The reaction was stirred vigorously at room temperature for 16 h. The solution was acidified to pH 2 and diluted with water and CH$_2$Cl$_2$. The phases were separated and the aqueous layer was extracted with EtOAC (3×10 mL) and the combined organic fractions were washed with water (10 mL), washed with brine (10 mL), dried over MgSO$_4$, filtered, and concentrated to give the title compound as a tan solid (0.29 g, 91%): mp 228-233° C.; $^1$H NMR (400 MHz, DMSO-d$_6$) δ 10.55-10.24 (m, 1H), 9.46 (s, 1H), 8.23 (d, J=8.0 Hz, 2H), 8.09 (d, J=7.9 Hz, 4H), 7.64 (d, J=8.5 Hz, 2H); ESIMS m/z 350 ([M+H]$^+$).

Example 10

Preparation of 4-(1-(4-(perfluoroethoxy)phenyl)-1H-1,2,4-triazol-3-yl)benzoic acid (Alternative to Example 7)

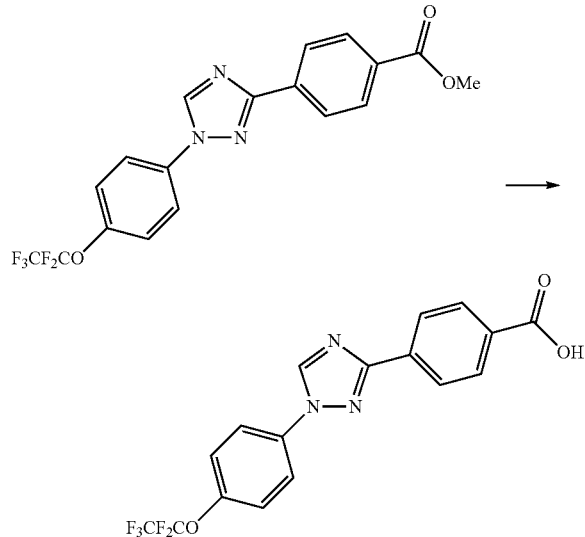

In a 250 mL round bottomed flask equipped with an overhead stirrer, T-type thermocouple, and nitrogen inlet were added methyl 4-(1-(4-(perfluoroethoxy)phenyl)-1H-1,2,4-triazol-3-yl)benzoate (11.1 g, 26.9 mmol) and THF (100 mL). To this yellow suspension were added water (10 mL) and lithium hydroxide-monohydrate (LiOH.H$_2$O; 3.4 g, 81 mmol). The reaction was stirred at 23° C. for 39 h during which time it became a yellow solution. The solution was warmed to 60° C. and stirred at 60° C. until complete by LC-MS. The reaction was cooled to 4° C. in an icebath and water (100 mL) was added to give a light yellow solution. Concentrated HCl (8.0 g) was added (note: exothermic) resulting in a thick white precipitate. The white suspension was stirred at 5° C. for 30 min and then the solid was collected by vacuum filtration. The filter cake was washed with water (2×25 mL), air dried for 3 h, and dried under vacuum (700 mm Hg) at 50° C. for 16 h to give the title compound as a white solid (10.3 g, 96%): mp 227-229° C.; $^1$H NMR (400 MHz, CDCl$_3$) δ 8.65 (s, 1H), 8.32 (d, J=8.4 Hz, 2H), 8.23 (d, J=8.4 Hz, 2H), 7.84 (d, J=8.9 Hz, 1H), 7.42 (d, J=8.9 Hz, 2H).

Example 11

Preparation of (4-(perfluoroethoxy)phenyl)hydrazine hydrochloride

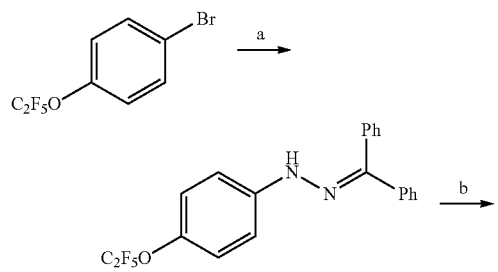

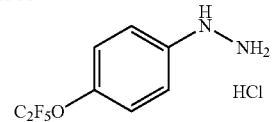

Step 1. Preparation of 1-(diphenylmethylene)-2-(4-(perfluoroethoxy)phenyl)-hydrazine: To a dry 2 L round bottomed flask fitted with an overhead mechanical stirrer, nitrogen inlet, thermometer, and reflux condenser were added 1 bromo-4-(perfluoroethoxy)-benzene (100 g, 344 mmol), benzophenone hydrazone (74.2 g, 378 mmol), and (2,2'-bis(diphenylphosphino)-1,1'-binaphthyl) (BINAP, 4.28 g, 6.87 mmol), and the mixture was suspended in anhydrous toluene (500 mL). To exclude oxygen, argon was sparged into the mixture for ten minutes (min) prior to and during the addition of palladium (II) acetate (Pd(OAc)$_2$, 1.54 g, 6.87 mmol) and sodium tert-butoxide (NaO$^t$Bu, 49.5 g, 515 mmol), which was added in portions. The argon sparge was halted and the brown mixture was warmed to 100° C. and stirred for 3 h. The reaction was cooled to RT and poured into water (500 mL) and the aqueous mixture was extracted with EtOAc (3×200 mL). The combined organic extracts were washed with water, washed with saturated aqueous NaCl, dried over anhydrous MgSO$_4$, filtered, and concentrated under reduced pressure on a rotary evaporator. The crude product was purified by flash column chromatography using 0-100% (v/v) EtOAc/hexanes as eluent to give the title compound as a red oil (123.3 g, 88%): $^1$H NMR (400 MHz, CDCl$_3$) δ δ 7.63-7.56 (m, 4H), 7.55 (t, J=1.5 Hz, 1H), 7.51 (d, J=4.7 Hz, 1H), 7.36-7.26 (m, 5H), 7.13-7.04 (m, 4H); $^{19}$F NMR (376 MHz, CDCl$_3$) δ −85.94, −87.84; $^{13}$C NMR (101 MHz, CDCl$_3$) δ 145.23, 143.46, 141.24, 138.06, 132.53, 129.74, 129.41, 129.03, 128.30, 128.23, 126.57, 122.82, 113.45.

Step 2. Preparation of (4-(perfluoroethoxy)phenyl)hydrazine hydrochloride: To a dry 250 mL round bottomed flask equipped with a magnetic stir bar, thermometer, and reflux condenser were added 1-(diphenylmethylene)-2-(4-(perfluoroethoxy)phenyl)hydrazine (63.6 g, 157 mmol), EtOH (50 mL), and concentrated HCl (100 mL, about 1.20 mol), and the reaction was warmed to 85° C. and stirred for 5 h. The reaction was cooled to RT and the dark slurry was concentrated to a brown paste on a rotary evaporator. The paste was slurried in CH$_2$Cl$_2$ (200 mL) and the resulting solid was collected by vacuum filtration and dried under vacuum at 40° C. to give the title compound as a tan solid (36.0 g, 82%): $^1$H NMR (400 MHz, DMSO-d$_6$) δ 10.47 (s, 3H), 8.62 (s, 1H), 7.43-7.18 (m, 2H), 7.20-6.93 (m, 2H); $^{19}$F NMR (376 MHz, DMSO-d$_6$) δ −85.30, −87.02; ESIMS m/z 243.15 ([M+H]$^+$).

What is claimed is:
1. A process for preparing a compound of the formula 3.2

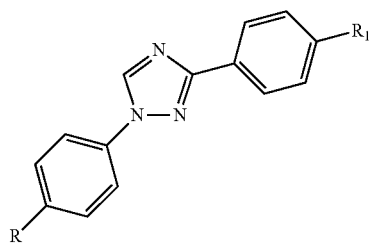

wherein R is a ($C_1$-$C_6$)haloalkoxy, and $R^1$ is —$NO_2$, —C(O)OH or —C(O)O($C_1$-$C_6$)alkyl comprising the step of contacting a compound of the formula 2.1

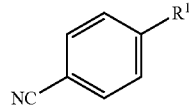

2.1 with an anhydrous inorganic acid in the presence of a polar, protic solvent to provide an imidate salt of the formula 2.2

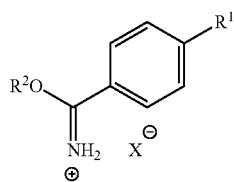

2.2 wherein $R^1$ is —$NO_2$, —C(O)OH or —C(O)O($C_1$-$C_6$)alkyl;

$R^2$ is ($C_1$-$C_6$)alkyl; and $X^\ominus$ is a counter ion of an inorganic acid.

2. The process of claim 1 for preparing a compound of the formula 3.2

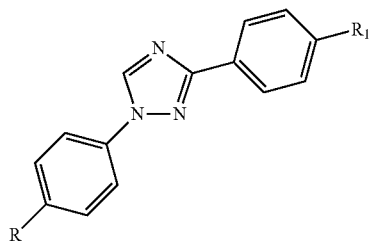

3.2 wherein R is a ($C_1$-$C_6$)haloalkoxy, and $R^1$ is —$NO_2$, —C(O)OH or —C(O)O($C_1$-$C_6$)alkyl, further comprising the step of contacting the imidate salt of the formula 2.2

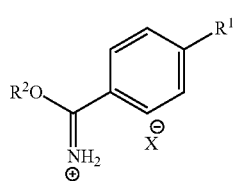

2.2 wherein $R^1$ is —$NO_2$, —C(O)OH or —C(O)O($C_1$-$C_6$)alkyl;

$R^2$ is ($C_1$-$C_6$)alkyl; and $X^{63}$ is a counter ion of an inorganic acid, with a compound of the formula 1.2

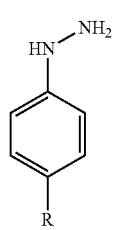

1.2 or a salt thereof, wherein R is a ($C_1$-$C_6$)haloalkoxy, in the presence of a weakly alkaline, heterocyclic solvent, or a non-basic, polar, aprotic solvent and a base, to provide an iminohydrazine compound of the formula 3.1

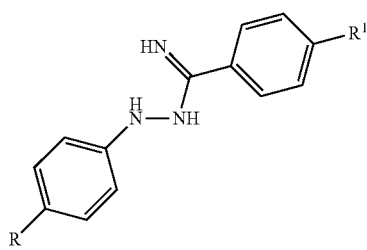

3.1 wherein R is a ($C_1$-$C_6$)haloalkoxy, and $R^1$ is —$NO_2$, —C(O)OH or —C(O)O($C_1$-$C_6$)alkyl.

3. The process of claim 2 for preparing a compound of the formula 3.2

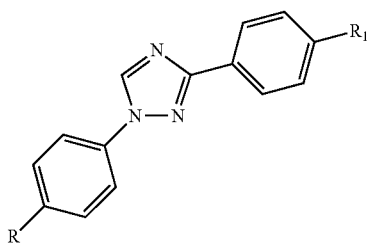

3.2 wherein R is a ($C_1$-$C_6$)haloalkoxy, and $R^1$ is —$NO_2$, —C(O)OH or —C(O)O($C_1C_6$)alkyl, further comprising the step of contacting the iminohydrazine compound of the formula 3.1

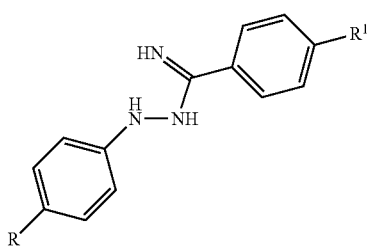

3.1 wherein R is a ($C_1$-$C_6$)haloalkoxy, and $R^1$ is —$NO_2$, —C(O)OH or —C(O)O($C_1$-$C_6$)alkyl, with a formate source to provide a compound of the formula 3.2

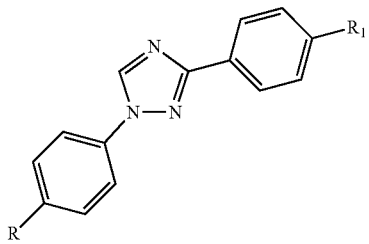

wherein R is a (C₁-C₆)haloalkoxy, and R¹ is —NO₂, —C(O)OH or —C(O)O(C₁-C₆)alkyl.

4. The process of claim 1, wherein the anhydrous inorganic acid is selected from the group consisting of HF, HCl, HBr and HI.

5. The process of claim 4, wherein the anhydrous inorganic acid is HCl or HBr.

6. The process of claim 5, wherein the polar, protic solvent is an alcohol solvent.

7. The process of claim 6, wherein the alcohol solvent is methanol, ethanol, n-butanol, iso-propanol, or a mixture thereof.

8. The process of claim 1, wherein R¹ is —C(O)OMe.

9. The process of claim 1, wherein R¹ is —C(O)OEt.

10. The process of claim 1, wherein R² is methyl.

11. The process of claim 1, wherein R² is ethyl.

12. The process of claim 1, wherein the anhydrous inorganic acid of step (a) is generated in situ by contacting an acyl halide with an alcohol.

13. The process of claim 1, wherein the anhydrous inorganic acid of step (a) is generated in situ by contacting thionyl chloride with an alcohol.

14. The process of claim 3 for preparing a compound of the formula 3.2 further comprising the step of contacting a

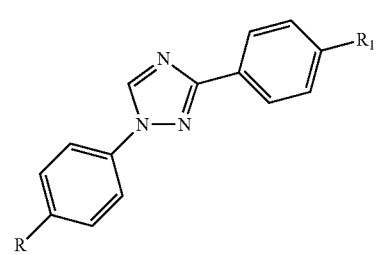

wherein R is a (C₁-C₆)haloalkoxy, and R¹ is —NO₂, —C(O)OH or —C(O)O(C₁-C₆)alkyl, further comprising the step of contacting a haloalkoxyaniline of Formula 1

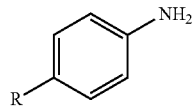

with sodium nitrite to produce an intermediate diazonium salt of Formula 1.1

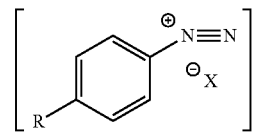

followed by reducing the intermediate diazonium salt of Formula 1.1 to produce a haloalkoxyarylhydrazine salt of Formula 1.2

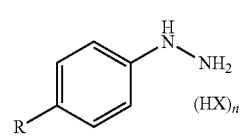

wherein R is (C₁-C₆)haloalkoxy; and n is 0, 1, or 2.

15. The process of claim 14, wherein the molar ratio of haloalkoxyanaline to sodium nitrite is from about 1:1 to about 1:2.

16. The process of claim 14, wherein the step of contacting haloalkoxyanaline with sodium nitrite is carried out in a polar, protic solvent.

17. The process of claim 14, wherein the step of contacting haloalkoxyanaline with sodium nitrite is carried out in the presence of an inorganic acid.

18. The process of claim 17, wherein the inorganic acid the step of contacting haloalkoxyanaline with sodium nitrite is selected from the group consisting of HCl, HNO₃, H₃PO₄, H₂SO₄, H₃BO₃, HF, HBr, HClO₄ and HBF₄.

19. The process of claim 14, wherein the pH of the step of contacting haloalkoxyanaline with sodium nitrite is about −1 to about 4.

20. The step of claim 14, wherein the temperature of the step of contacting haloalkoxyanaline with sodium nitrite is about −10° C. to about 5° C.

* * * * *